United States Patent [19]
Miller

[11] Patent Number: 5,878,749
[45] Date of Patent: Mar. 9, 1999

[54] NON-INVASIVE METHODS AND APPARATUS FOR IN VIVO MEASUREMENT OF INTRA-VARICEAL PRESSURE AND WALL TENSION

[75] Inventor: Larry S. Miller, Bala Cynwyd, Pa.

[73] Assignee: Temple University—of the Commonwealth System Of Higher Education, Philadelphia, Pa.

[21] Appl. No.: 691,103

[22] Filed: Aug. 1, 1996

[51] Int. Cl.$^6$ .................................................. A61B 19/00
[52] U.S. Cl. ........................... 128/898; 600/455; 600/462
[58] Field of Search .......................... 128/660.01–660.02, 128/661.07, 661.09, 662.06, 898, 207.14–207.16, 669, 672; 606/140; 600/454, 455, 462 468

[56] References Cited

U.S. PATENT DOCUMENTS

| | | | |
|---|---|---|---|
| 4,582,067 | 4/1986 | Silverstein et al. | 128/661.09 |
| 4,770,185 | 9/1988 | Silverstein et al. | 128/661.08 |

OTHER PUBLICATIONS

Miller, et al., "Simultaneous High–Frequency Esophageal Ultrasound and Mamometry in Normal Volunteers," Gastroenterology, vol. 103, p. A147 (Apr., 1993).

Nevens et al. "Measurement of variceal pressure and its clinical implications." Scand. J. Gastroenterol. 29(Suppl. 207):6–10, 1994.

Nevens et al. "Measurement of cariceal pressure with an endoscopic pressure sensitive gauge." J. Hepatol. 24(1):66–73, 1996.

*Primary Examiner*—Mickey Yu
*Assistant Examiner*—Kelly O'Hara
*Attorney, Agent, or Firm*—Schnader Harrison Segal & Lewis LLP

[57] ABSTRACT

A method for evaluating a varix, including the steps of: (a) placing a system for observing whether the varix is open or closed into a region adjacent to the varix; (b) placing a system for sensing pressure into a region adjacent to the varix; (c)temporarily increasing the pressure in the region adjacent to the varix so that the varix collapses; (d) simultaneously observing the varix with the observing system and monitoring the pressure in the region adjacent to the varix with the pressure sensing system when the varix closes or reopens. Also, a device for evaluating a varix, including: (a) a system for observing whether the varix is open and generating an observing system output; and (b) a system for sensing the pressure in the region adjacent to the varix and generating a pressure sensing output.

13 Claims, 5 Drawing Sheets

NON-INVASIVE METHODS AND APPARATUS FOR IN VIVO MEASUREMENT OF INTRA-VARICEAL PRESSURE AND WALL TENSION

BACKGROUND OF THE INVENTION

1. Field of the Invention

The present invention relates to methods for diagnosing, monitoring and treating varices, and, in particular, to methods for non-invasive measurement of intra-variceal pressure and wall tension.

2. Description of the Related Art

Esophageal varices are one of the major causes of gastrointestinal bleeding. Varices are a frequent complication in patients with cirrhosis of the liver. Approximately 50,000 people in the United States are believed to suffer from esophageal varices each year. Of those, 35,000 people experience severe bleeding episodes, half of which are fatal.

Because of the severity of the outcome of gastrointestinal bleeding, many physicians favor prophylactic pharmacologic intervention with β-blockers immediately after diagnosis of varices. Endoscopic sclerotherapy, balloon tamponade, pharmacologic therapy with vasopressives, nitrates, and somatostatin, transjugular intra-hepatic portal systemic hunts, and surgical portal systemic shunts are most frequently used once bleeding episodes are detected.

In order to determine which course of treatment is appropriate and to monitor the progress and effectiveness of that treatment, it is necessary to objectively evaluate and monitor the varices. Unfortunately, however, other than through direct observation of re-bleeding, or lack thereof, monitoring progress and recovery of varices is extremely difficult. Existing methods for monitoring varices, such as, esophagoscopy, have proven unreliable and inadequate.

While it is believed that variceal size, intra-variceal pressure and wall tension are the critical measures of the severity of an existing varix, it has not been possible to accurately and safely measure any of these variables in vivo. Known methods for measuring intra-variceal pressure involve actually puncturing the varix with a needle to take an intra-variceal pressure reading. This is a relatively high risk procedure with frequent complications, including severe bleeding. In addition, there are no known means for accurately determining the radius or the wall thickness of varices in vivo.

It is accordingly an object of this invention to overcome the disadvantages and drawbacks of the known art and to provide methods for safely and accurately diagnosing, monitoring and treating esophageal varices.

It is a further object of this invention to provide methods for non-invasive in vivo determination of variceal pressure, size and wall thickness.

It is a further object of this invention to provide methods for the in vivo measurement of variceal wall tension.

Further objects and advantages of this invention will become apparent from the detailed description of a preferred embodiment which follows.

SUMMARY OF THE INVENTION

The present invention is directed to a method for evaluating a varix, comprising the steps of: (a) placing means for observing whether the varix is open or closed into a region adjacent to the varix; (b) placing means for sensing pressure into a region adjacent to the varix; (c) temporarily increasing the pressure in the region adjacent to the varix so that the varix collapses; and (d) simultaneously observing the varix with the observing means and monitoring the pressure in the region adjacent to the varix with the pressure sensing means when the varix closes or reopens.

The present invention is also directed to a device for evaluating a varix, comprising: (a) means for observing whether the varix is open and generating an observing means output; and (b) means for sensing the pressure in the region adjacent to the varix and generating a pressure sensing output.

BRIEF DESCRIPTION OF THE DRAWINGS

Other objects, features, and advantages of the present invention will become more fully apparent from the following detailed description of the preferred embodiment, the appended claims, and the accompanying drawings in which:

DESCRIPTION OF THE PREFERRED EMBODIMENT(S)

Methods for evaluating varices in accordance with the present invention include steps of: (a) inserting means for observing whether the varix is open or closed into a region adjacent to the varix; (b) inserting means for sensing pressure into a region adjacent to the varix; (c) observing the resting pressure in the region adjacent to the varix; (d) temporarily increasing the pressure in the region adjacent to the varix so that the varix collapses; (e) observing the varix with the observing means and monitoring the pressure in the region adjacent to the varix with the pressure sensing means when the varix closes or reopens; and (f) calculating the intra-variceal pressure, the transmural pressure and/or the wall tension.

In accordance with the present invention, the observing means and the pressure sensing means are inserted into the region adjacent to the varix. Where the observing means is an ultrasound system as described below the observing means and pressure sensing means are preferably positioned adjacent to the varix in a region where the varix is relatively circular to avoid tangential imaging. Where the observing means is a doppler transducer as described below the observing means and pressure sensing means are preferably positioned so that the doppler transducer is coupled acoustically with the varix. Once the observing means and the pressure sensing means are properly positioned, the resting pressure in the region adjacent to the varix may be observed. The varix is then collapsed by temporarily increasing the external pressure on the varix. Where the varix is in the esophagus, the pressure increase may be accomplished by having the subject swallow a bolus of liquid (about 10 ml), such as water or gelatin. Alternatively, the pressure increase may be generated by inflating an expandable member, such as an inflatable bladder adjacent to the varix.

When the pressure in the region adjacent to the varix exceeds the intra-variceal pressure, the varix will collapse temporarily. As the pressure returns to normal, the varix and the pressure in the region adjacent to the varix are observed simultaneously using the varix observing means and the pressure sensing means.

Where the observing means is an ultrasound system, the closing or reopening of the varix may be observed visually on the ultrasound video display. Where the observing means is a doppler transducer system, the closing or reopening of the varix may be observed either aurally or visually when the doppler transducer amplifies the sound of the resumption of blood flow through the varix or when the doppler transducer flow signal returns on a monitoring device.

Figure 2A:
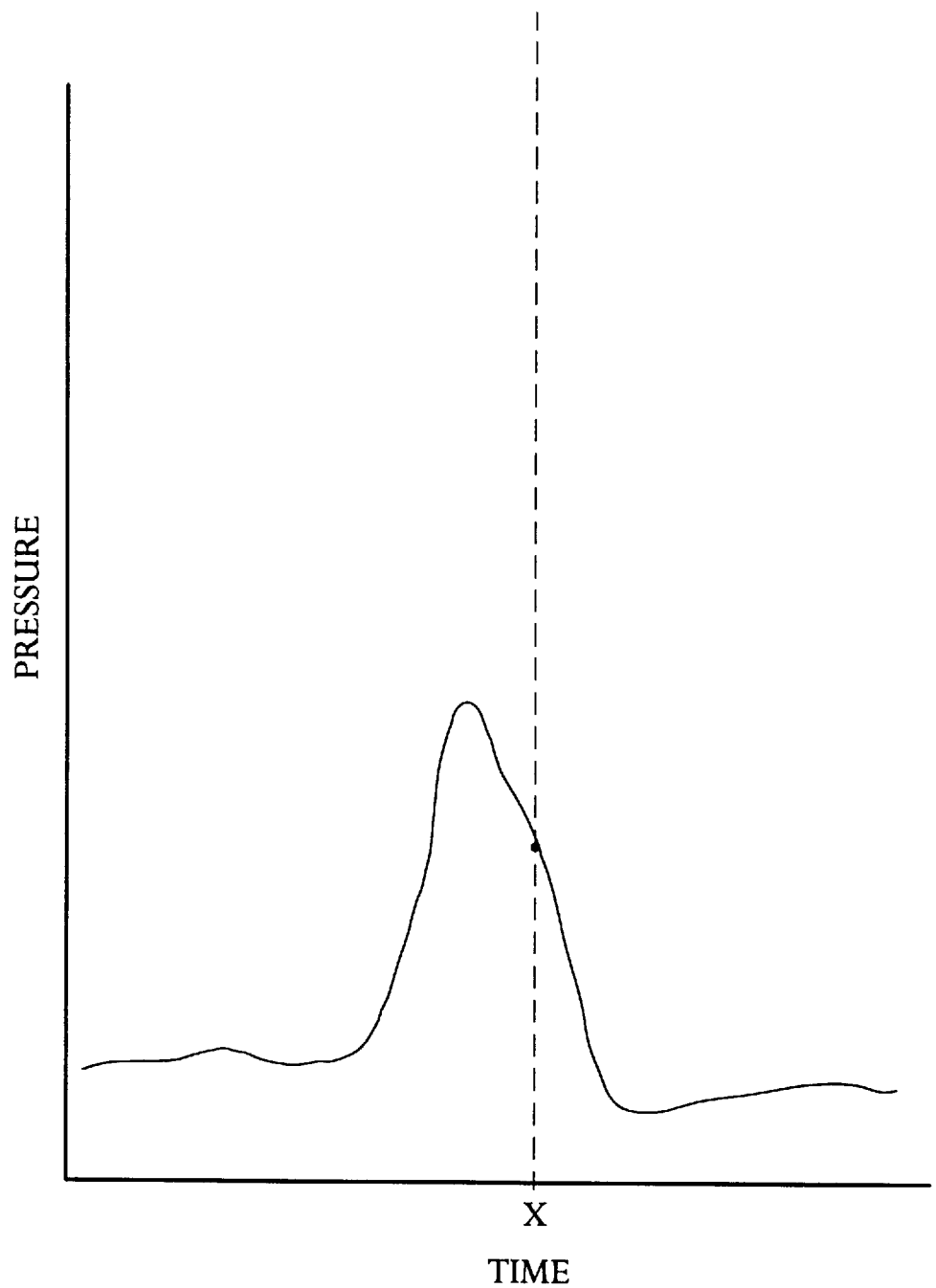
FIG. 2A shows a manometry output and FIG. 2B shows a corresponding display of an ultrasound image.
Figure 2B:
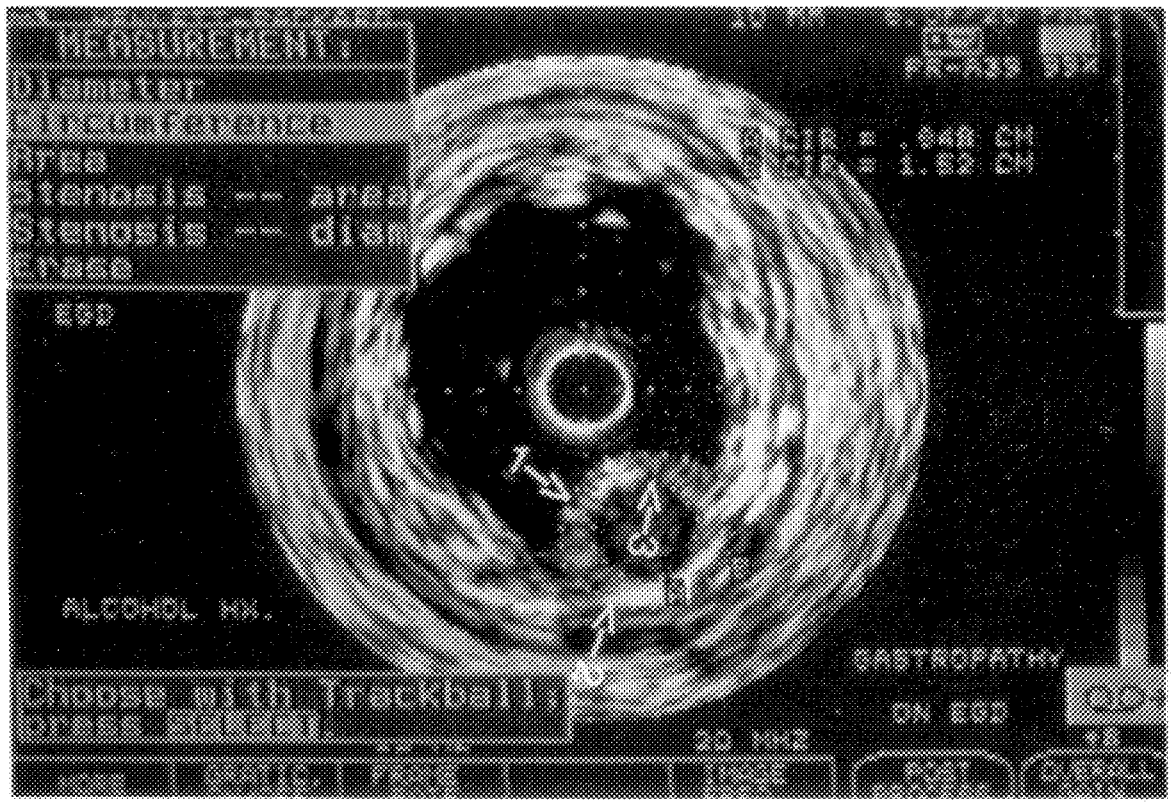

The intravariceal pressure is the pressure observed either when the varix closes or when the varix reopens. The transmural pressure may be calculated by determining the difference between the pressure in the region adjacent to the varix at rest and the pressure at which the varix closes or reopens and determining the difference. The pressure at which the varix closes or reopens is measured by observing the recorded pressure readings simultaneously with the output of the varix observing means. Where the output of the varix observing means is a visual display, such as the ultrasound image described below, the display is preferably observed at a reduced speed or on a frame by frame basis. FIG. 2; shows a simplified diagram of a computer screen showing one frame of an ultrasound image at time "x" as indicated on the adjacent manometry output, FIG. 2. Similarly, where the observing means is a doppler transducer, the doppler transducer output may be recorded and observed in a visual format at a reduced speed.

The results of the foregoing may then be used to evaluate the varix. It is believed that the risk of variceal bleeding and rupture increase with increased variceal wall tension and/or transmural wall pressure. Variceal wall tension is defined as an inwardly directed force that opposes an outwardly directed expanding force in the variceal wall. Rupture of the varix occurs when the expanding force exceeds the vessel's maximal wall tension. Accordingly, these factors may be used to evaluate varices in accordance with the present invention by use of the Laplace equation as follows:

$$T = tp(r_o/w),$$

where,

T=wall tension;

tp=transmural pressure between the varix and the esophageal lumen;

$r_o$=outer radius of the varix; and w=wall thickness of the varix.

The inner and outer radii of the varix may be calculated as follows:

$$r_o = C_o/2\pi$$

$$r_i = C_i/2\pi,$$

where, $C_o$=outer circumference of the varix; and $C_i$=inner circumference of the varix.

As shown in FIG. 2D, the outer circumference is preferably measured at the border between the hypoechoic fluid-filled esophageal lumen and the hyperechoic mucosa where the varix protrudes into the esophageal lumen 1. In the intra-mural portion of the varix, the outer circumference is preferably measured at the border between the hyperechoic submucosa and the hypoechoic muscularis propria 2. The inner circumference is preferably measured at the border of the hypoechoic blood-filled variceal lumen and the hyperechoic inner wall of the varix 3.

Wall thickness (w) may be calculated as follows:

$$w = (C_o - C_i)/2\pi.$$

In a preferred embodiment of the present invention, the variceal wall tension may be evaluated at any region of the esophagus, but most importantly in the region where the varix appears largest. In addition, variceal wall tension may be evaluated serially after therapeutic intervention to monitor the progress of the therapy.

Where the varix observing means produces a visual image of the varix, such as with an ultrasound device, both the transmural pressure and the wall tension may be observed. Where the varix observing means does not produce a visual image of the varix, only the transmural pressure may be determined, unless separate means are employed to determine the dimensions of the varix.

The present invention also comprises devices for performing the steps of the foregoing methods. Devices for performing the steps of the foregoing methods comprise: (a) means for observing whether the varix is open and generating an observing means output and (b) means for sensing the pressure in the region adjacent to the varix and generating a pressure sensing output. In addition, devices for performing the steps of the foregoing methods may also include means for increasing the pressure in the region adjacent to the varix; and means for recording and displaying the output of the observing means and the pressure sensing means.

Figure 1:
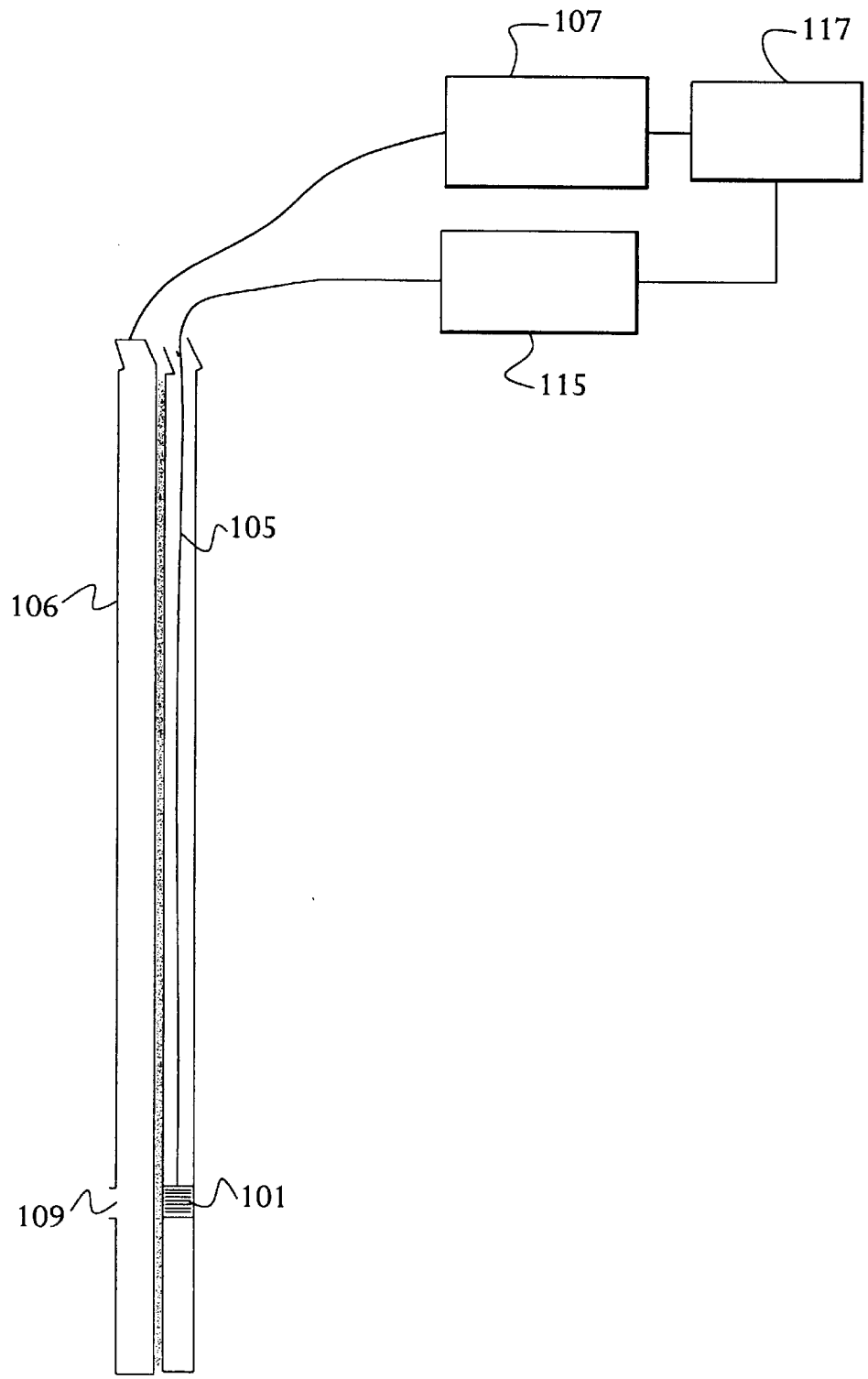
FIG. 1 shows a schematic side view of a device in accordance with the present invention.

Referring now to FIG. 1, the observing means 101 may be an ultrasound imaging device, preferably a high frequency ultrasound transducer, such as the 20-MHZ ultrasound transducer manufactured by Endosound/Microvasive or Olympus. Where the observing means 101 is an ultrasound system, the system preferably comprises a transducer that rotates within a catheter 105 to produce a real-time 360° cross-sectional ultrasound image. Imaging may be performed on any suitable imaging device 115, such as the Intrasonics Ultrasound device manufactured by Diasonics, or an intra-vascular ultrasound device, such as that manufactured by Hewlett Packard or Olympus, and may be recorded with any suitable recording means 117, such as a Synectics Manometry/Video computer system or the Panasonic digital AV mixer, part no. WJ-AVE7.

Figure 4:
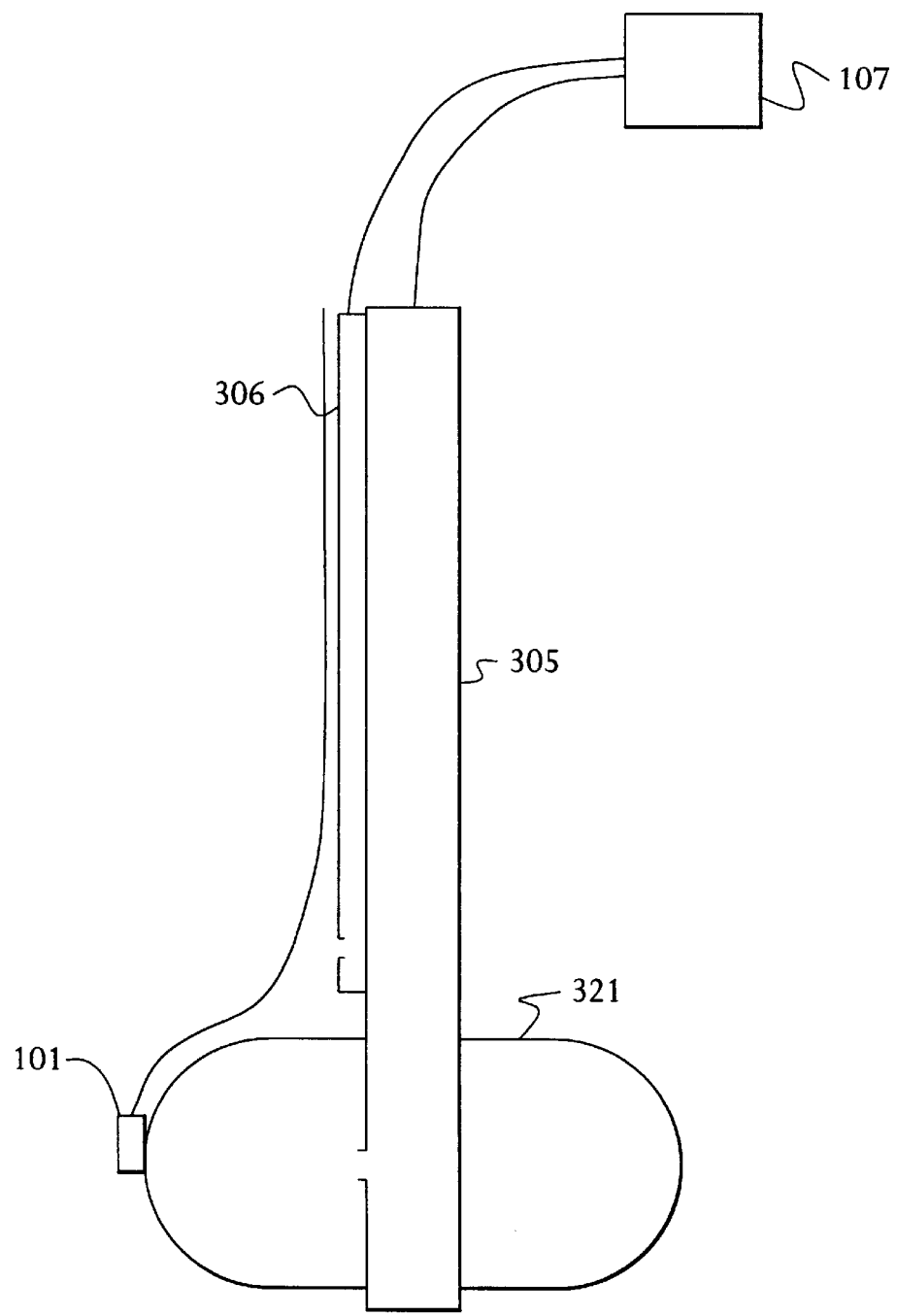
FIG. 4 shows a schematic side view of another alternative embodiment of a device in accordance with the present invention.

Alternatively, the observing means 101 may be a doppler transducer, such as the Microvascular Doppler Sonography (MF20), a pulsed doppler method with 20 MHZ which is able to measure velocity and direction of flow, as described in Kanaya et al., Transendoscopic Microvascular Doppler Sonography for the Assessment of Hemodynamics of Esophageal and Gastric Varices, Journal of Japan Surgical Society 96(2):106–15, 1995 February. The doppler transducer output may also be recorded with any suitable standard recording means 117. As shown in FIG. 4, where the observing means 101 is a doppler transducer, the doppler transducer may be positioned inside or outside the catheter 105 and inside or outside any inflatable member so long as the doppler transducer may be acoustically coupled with the varix during the procedure.

The pressure sensing means 107, is preferably a standard manometry system, such as the water perfused manometry system manufacture by Narco Arndorfer or a solid state system such as that manufactured by Synectics. The port 109 or the solid state manometry transducer (not shown) of the pressure sensing means 107 is preferably positioned adjacent to the observing means 101 to enable the device to record the pressure and the status of the varix at the same position.

FIG. 1, shows a dual catheter or dual lumen catheter system in accordance with the present invention in which a first catheter 105 contains an ultrasound transducer coupled to imaging means 115 and recording means 117. The second catheter 106 has a port 109 open to the lumen and is coupled to a manometry system such as pressure sensing means 107 and the recording means 117. The port 109, or in an alternative embodiment, the manometry transducer, is positioned adjacent to the observing means 101, which can be an ultrasound transducer. In an alternative embodiment (not shown), the device may consist of a single dual lumen catheter housing both the observing means 101 and the pressure sensing means 107. In yet another alternative embodiment (not shown), a solid state manometry transducer may be positioned in the ultrasound catheter, adjacent to the ultrasound transducer.

Figure 3:
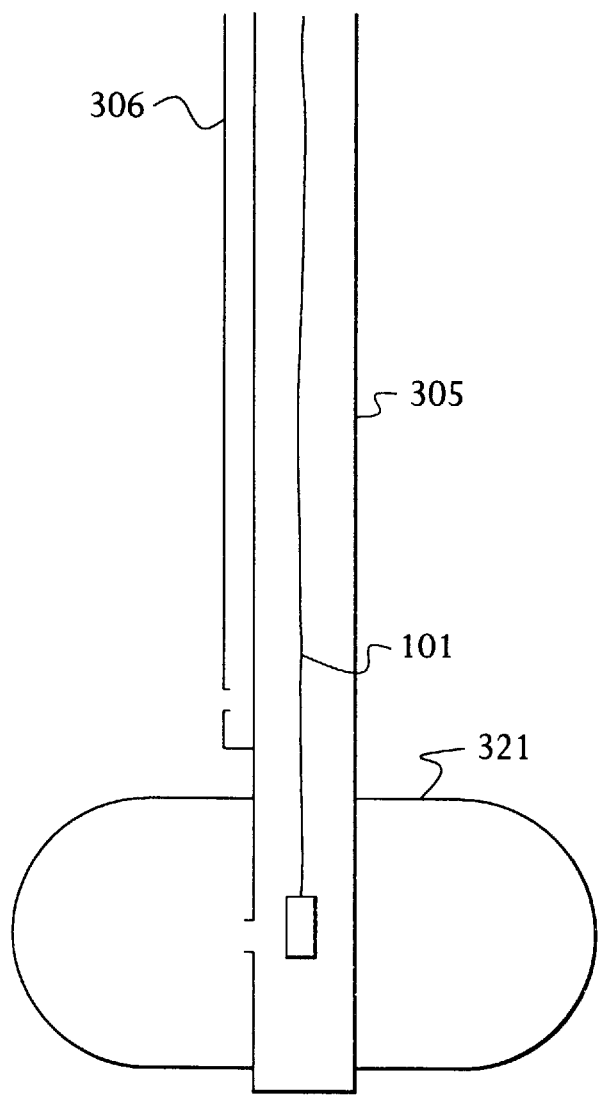
FIG. 3 shows a schematic side view of an alternative embodiment of a device in accordance with the present invention.

Referring now to FIGS. 3 and 4, an alternative embodiment of the present invention employs an expandable member 321, such as an inflatable bladder, to increase the pressure on the varix. The inflatable bladder may be a balloon such as the endoscopic balloon for measurement of variceal pressure developed by Gertsch et al., and described in Manometry of Esophageal Varices, Comparison of Endoscopic Balloon Technique wit Needle Puncture, Gastro., 105: 1159–1166, 1993. A manometry system 107 is coupled to the expandable member 321 by way of a catheter 305 and senses the pressure in the expandable member 321. In addition, a second manometry catheter 325 may be positioned outside the expandable member 321 and coupled to the manometry system 107 to sense the lumenal pressure. The expandable member 321 is preferably filled with a fluid such as water so as not to interfere with the varix observing means 101. Where the varix observing means 101 is an ultrasound transducer or doppler transducer, the transducer may be positioned either inside the expandable member 321, as shown in FIG. 3, or outside the expandable member 321, as shown in FIG. 4.

Both the observing means 101 and the pressure sensing means 107 are preferably coupled to a simultaneous recording system, such as the Synectics or Panasonic systems described above to permit simultaneous recordation of the manometry system output and the ultrasound image or doppler transducer output and thereby to permit temporal correlation and simultaneous display of the ultrasound image or doppler transducer output and the manometry output as shown in FIGS. A and B.

The full catheter assembly may be placed into the esophagus transnasally, transorally, or through a fiberoptic or video endoscope.

It will be understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A method for evaluating an esophageal varix, comprising the steps of:
   (a) placing transnasally, into a region adjacent to the esophageal varix, means for observing whether the esophageal varix is open or closed;
   (b) placing transnasally, into a region adjacent to the esophageal varix, means for sensing pressure;
   (c) temporarily increasing the pressure in the region adjacent to the esophageal varix so that the esophageal varix collapses; and
   (d) simultaneously observing the esophageal varix with the observing means and monitoring the pressure in the region adjacent to the esophageal varix with the pressure sensing means when the esophageal varix closes or reopens.

2. The method of claim 1, wherein step (d) comprises the step of displaying the pressure sensing means output simultaneously with the observing means output.

3. The method of claim 2, further comprising the step of observing the resting pressure in the region adjacent to the esophageal varix.

4. The method of claim 3, wherein the esophageal varix observing means is an ultrasound device generating an ultrasound image and the pressure sensing means is a manometry device.

5. The method of claim 4, further comprising the step of:
   (e) determining the transmural pressure from the manometry output by subtracting the resting pressure in the region adjacent to the esophageal varix from the pressure observed in step (d).

6. The method of claim 5, further comprising the steps of:
   (e) determining the radius of the esophageal varix from the ultrasound image;
   (f) determining the wall thickness of the esophageal varix from the ultrasound image; and
   (g) determining the transmural pressure from the manometry output by subtracting the resting pressure in the region adjacent to the esophageal varix from the pressure observed in step (d).

7. The method of claim 6, further comprising the step of:
   (h) determining the wall tension of the esophageal varix using the formula $T=tp(r_o/w)$;
   wherein, T=the wall tension of the varix, tp=the transmural pressure, $r_o$=the outer radius of the varix; and w=the wall thickness of the varix.

8. A transnasal device for evaluating an esophageal varix, comprising:
   (a) means for observing whether the esophageal varix is open and generating an observing means output; and
   (b) means for sensing the pressure in the region adjacent to the esophageal varix and generating a pressure sensing output.

9. The device of claim 8, further comprising:
   (c) means for simultaneously displaying the observing means output and the pressure sensing means output.

10. The device of claim 9, wherein:
    the observing means comprises an ultrasound device.

11. The device of claim 9, wherein:
    the observing means comprises a doppler transducer.

12. The device of claim 9, further comprising:
    (d) means for temporarily increasing the pressure in the region adjacent to the esophageal varix so that the esophageal varix collapses.

13. The device of claim 12, wherein:
    the pressure increasing means comprises an inflatable bladder.

* * * * *